US00PP17158P3

(12) United States Plant Patent
Parfitt et al.

(10) Patent No.: US PP17,158 P3
(45) Date of Patent: Oct. 17, 2006

(54) FEMALE PISTACHIO TREE NAMED 'GOLDEN HILLS'

(50) Latin Name: *Pistacia vera*
Varietal Denomination: Golden Hills

(75) Inventors: Dan E. Parfitt, Davis, CA (US); Joseph Maranto, Bakersfield, CA (US); Craig E. Kallsen, Bakersfield, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/086,170

(22) Filed: Mar. 21, 2005

(65) Prior Publication Data

US 2006/0212980 P1 Sep. 21, 2006

(51) Int. Cl.
*A01H 5/00* (2006.01)

(52) U.S. Cl. ..... Plt./152
(58) Field of Classification Search ..... Plt./152
See application file for complete search history.

(56) References Cited

PUBLICATIONS

U.S. Appl. No. 11/086,616, not yet published, Parfitt et al.
U.S. Appl. No. 11/085,894, not yet published, Parfitt et al.
Parfitt, D.E. et al. (1993) "Pistachio Cultivar Improvement: 1992," California Pistachio Industry, Annual Report, Crop Year 1992–93, p. 94.
Parfitt, D.E. et al. (1994) "Pistachio Cultivar Improvement: 1993," California Pistachio Industry, Annual Report, Crop Year 1993–94, pp. 98–99.
Parfitt, D.E. et al. (1995) "Pistachio Cultivar Improvement: 1994," California Pistachio Industry, Annual Report, Crop Year 1994–95, pp. 87–88.
Parfitt, D.E. et al. (1996) "Pistachio Cultivar Improvement: 1995," California Pistachio Industry, Annual Report, Crop Year 1995–96, pp. 90–98.
Parfitt, D.E. et al. (1997) "Pistachio Cultivar Improvement: 1996," California Pistachio Industry, Annual Report, Crop Year 1996–97, pp. 123–124.
Parfitt, D.E. et al. (1998) "Pistachio Cultivar Improvement: 1997," California Pistachio Industry, Annual Report, Crop Year 1997–98, pp. 134–142.
Parfitt, D.E. et al. (1999) "Pistachio Cultivar Improvement: 1998," California Pistachio Commission, 1998/99, Production Research Reports, pp. 230–279.
Parfitt, D.E. et al. (2000) "Pistachio Cultivar Improvement: 2000," California Pistachio Commission, 2000, Production Research Reports, pp. 303–304.
Parfitt, Dan E. et al. (1991) "Pistachio Cultivar Improvement—1990," California Pistachio Industry, Annual Report, Crop Year 1990–91, pp. 118–119.
Parfitt, Dan E. et al. (1992) "Pistachio Cultivar Improvement—1991," California Pistachio Industry, Annual Report, Crop Year 1991–92, pp. 163–164.
Parfitt, Dan E. et al. (1999) "Pistachio Cultivar Improvement: 1998," California Pistachio Industry, Annual Report, Crop Year 1998–1999, pp. 113–112.
Parfitt, Dan E. et al. (2000) "Pistachio Cultivar Improvement 1999," California Pistachio Industry, Annual Report, Crop Year 1999–2000, pp. 104–105.
Parfitt, Dan E. et al. (2001) "Pistachio Cultivar Improvement: 2000," California Pistachio Industry, Annual Report, Crop Year 2000–2001, pp. 141–142.

*Primary Examiner*—Kent Bell
*Assistant Examiner*—June Hwu
(74) *Attorney, Agent, or Firm*—Morrison & Foerster LLP

(57) ABSTRACT

A new and distinct variety of Pistachio tree denominated 'Golden Hills' is described. This selection's most significant advantage over the industry standard is the higher early yield and a greater percentage of this yield is composed of edible split nuts. This variety also has less of a chilling requirement for dormancy resulting in more uniform spring foliation, flowering, pollination and nut maturity at harvest.

12 Drawing Sheets

Botanical/commercial classification (*Pistacia vera*)/ new Pistachio variety.
Variety denomination: 'Golden Hills'.

BACKGROUND OF THE INVENTION

The present invention relates to a new and distinct variety of Pistachio tree *Pistacia vera* which has been denominated varietally as 'Golden Hills', and more particularly to such a pistachio tree which has a harvest date of two to thirteen days earlier than the industry standard pistachio tree variety 'Kerman'.

'Golden Hills' produces a greater yield and higher percentage of split, edible nuts than 'Kerman' while maintaining a similar low percentage of loose shells and kernels. The earlier harvest date will permit growers to extend their harvest period and reduce competition for scarce harvesting resources and may reduce disease in the northern production areas of California by permitting an earlier harvest before fall rains. The cultivar requires less chilling than 'Kerman', which improves uniformity of foliation, bloom, nut set, nut fill, and uniformity of nut maturity at harvest in years with insufficient chilling for 'Kerman'. Based on all of our evaluations, this cultivar appears to be an exceptional producer and has the potential to increase grower profits by up to 40%, while being better adapted to low chill years, more uniform harvest period, and having fewer Navel Orangeworm problems.

SUMMARY OF THE INVENTION

'Golden Hills' differs from 'Kerman' as follows: a) This cultivar produced 46% higher yield than 'Kerman' the primary cultivar grown on a commercial basis in California (<95% of the crop) and 43% greater yield in 2004; b) Nut size is on average slightly larger than 'Kerman' and weight is similar; c) Flowering and harvest are 2 to 4 weeks eariler than 'Kerman'. This earlier harvest date is important as it permits growers to more efficiently use their equipment and labor by spreading the harvest period across 6 weeks, rather than the current 3 week harvest period. Fruit ripening is also more uniform than was observed for 'Kerman'; d) Earlier harvest resulted in significantly less Navel Orangeworm damage (0.0% vs. 9.3%). This is an important characteristic since nut damage on the tree is associated with aflatoxin contamination; e) 'Golden Hills' had more but smaller scaffold branches than 'Kerman', producing a smaller more bushy tree after 3–4 years of training; and f) 'Golden Hills' buds were about 1 mm longer than 'Kerman' buds.

'Golden Hills' has been asexually reproduced in Kern County, Calif. and Madera County Calif. The cultivar was propagated from buds, inserted into both 'PG-1' and 'UCB-1' rootstocks (budded onto). The cultivar is present at field locations in Kern Co. and Madera Co. (test plots). In addition 2 trees have been budded on 'UCB-1' rootstocks in pots at Davis for planting into the field this spring. 'Golden Hills' is grafted onto 'UCB-1' rootstock in the field at the Wolfskill experimental farm near Winters at row 6, tree 16 A and B.

DETAILED BOTANICAL DESCRIPTION

The following description describes the key characteristics of a new female pistachio cultivar named 'Golden Hills' as well as reference to the standard pistachio cultivar 'Kerman' in California.

The Royal Horticultural Society color chart from 1986 is used in the identification of color. Also, common color terms are to be accorded their ordinary dictionary significance.

The cross: The cross that produced 'Golden Hills' was originally made in 1990, and the original seedling was planted at a research plot in 1991 near Bakersfield, Calif. The cross was made between a *Pistacia vera* female '2-35', located in Kern County and propagated from wood supplied to Joseph Maranto from a plot in UC Davis in 1985, and a *Pistacia vera* male 'ES#2' originally from Chico, CA. 'ES#2' is no longer available. This seedling, from this cross, was designated as B22-31. Buds from this seedling tree were budded to rootstocks planted in August 1997 in an advanced selection trial near Lost Hills, Calif. Each cultivar is represented by 2 replicates of 10 trees grafted to 'UCB-1' and 10 trees grafted to 'PG-1' per replicate. They first flowered in 2001. Performance data was obtained in 2002, 2003, and 2004. Nursery rootstock trees were budded with this selection in 1997 and were used to plant a second advanced selection trial in Madera County north of Fresno, Calif. in September 1999. Each plant selection is represented by two replicates of 5 trees grafted to 'UCB-1' and 5 trees grafted to 'PG-1' per replicate. This selection flowered and fruited in 2003. The cultivar is stable and no significant differences in morphological or phonological characteristics were observed when propagated on rootstocks.

Tree vigor: The tree is of average size for a pistachio, based on observation of 7 year old trees. Grafted trees are about 3 m tall at 7 years with a spread equal to the height. Trunk diameters are 10 to 15 cm.

Figure 2:
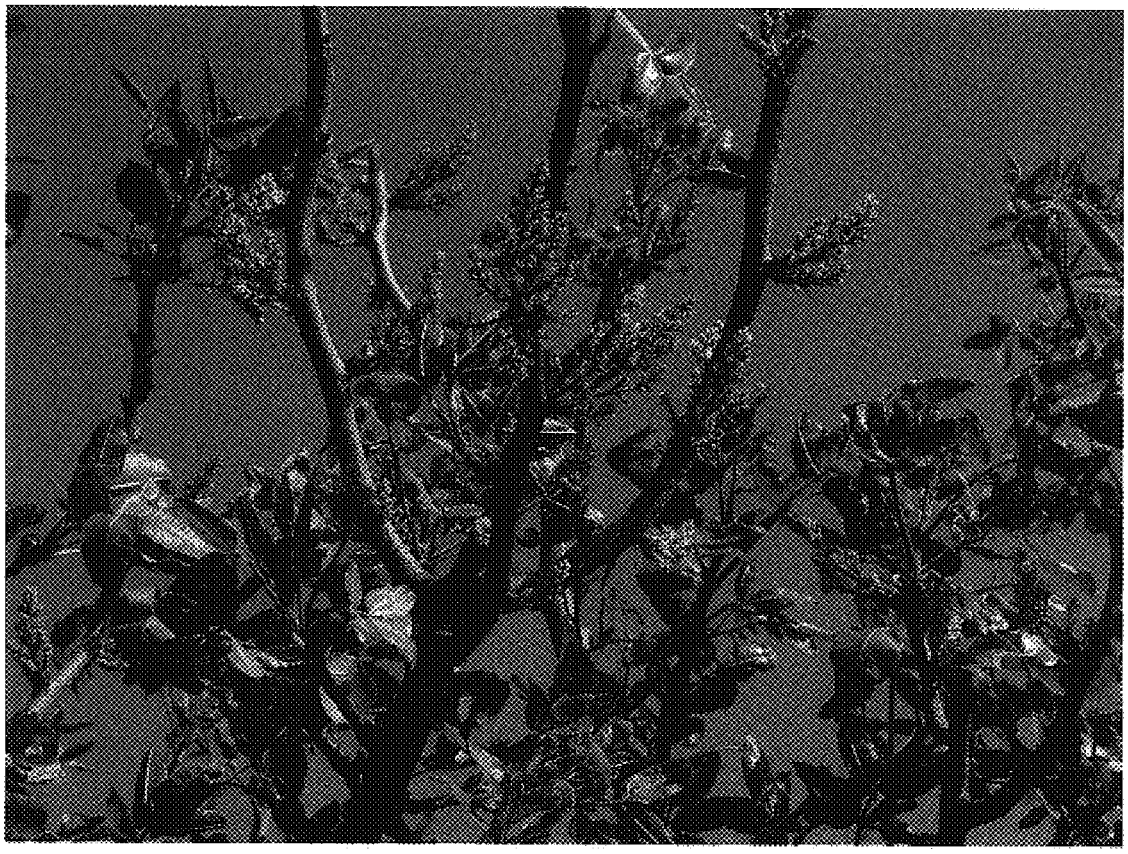
FIG. 2. 'Golden Hills' flowers—Mar. 31, 2004. Several days ahead of 'Kerman'. Some flowers have set.
Figure 6:
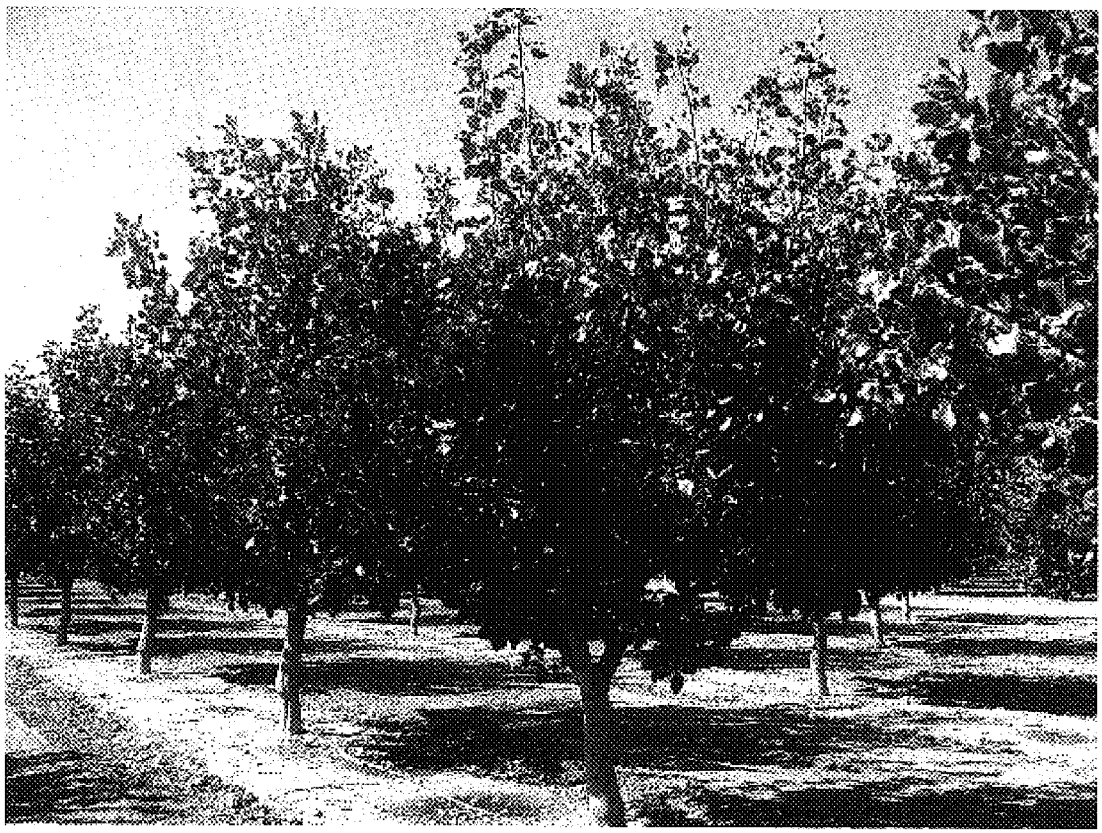
FIG. 6. 'Golden Hills' trees at Bakersfield test plot, 2003.

Tree structure: 'Golden Hills' has tree structure and branching habit typical for *Pistacia vera* L. Branch angles are broad, ranging from 80 to 90 degrees for both scaffold and lateral branches. Distribution of scaffold and lateral branches are a function of pruning and training activities which are practiced intensively during the first three years of growth (FIGS. 2 and 6).

Figure 13:
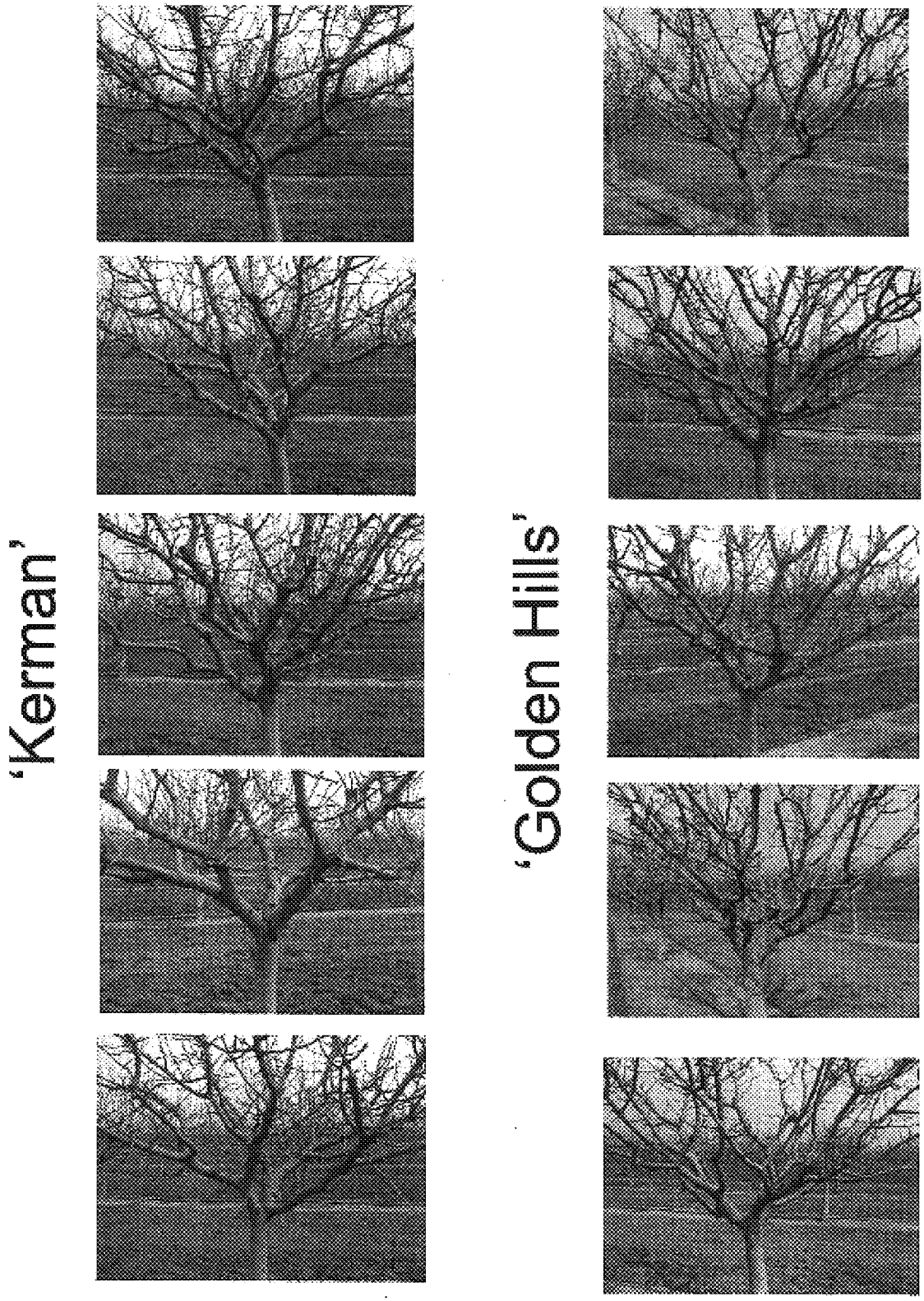
FIG. 13. 5 trees each of 'Kerman' and 'Golden Hills', showing the difference in scaffold branch development. This results in a smaller, shrubbier tree for 'Golden Hills'.

'Golden Hills' had more but smaller scaffold branches than 'Kerman', producing a smaller more bushy tree after 3–4 years of training. The effect is clearly shown in FIG. 13, where photos of 5 trees each of 'Golden Hills' and 'Kerman' are presented. This is a significant character, since it may help explain the excellent yield characteristics of 'Golden Hills'. The shrubbier tree has more fruit bearing wood and also probably puts fewer resources into wood development and more resources into fruit development. This type of tree may also require less extensive pruning in later years, resulting in cost savings to the grower.

Bark: 'Golden Hills' bark color was identical to the bark color of 'Kerman', specifically RHS 202D (grey).

Figure 14:
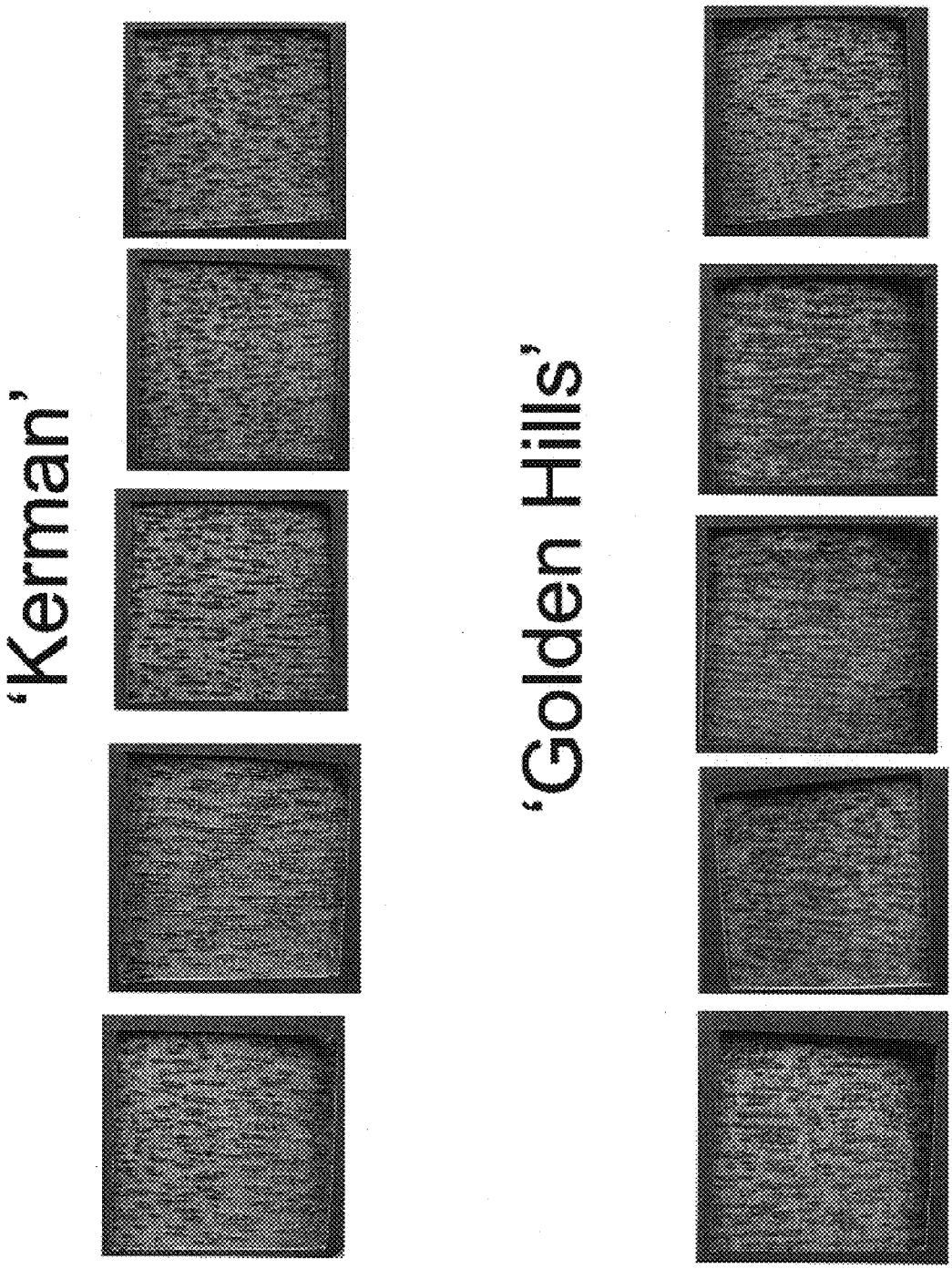
FIG. 14. Lenticel pictures from each of 5 trees for 'Kerman' and 'Golden Hills'. The areas shown are 25 sq. cm., 5 cm on each side.

Trunk Lenticels: Close up photo evaluation of trunk lenticels was undertaken. There were visible differences between the lenticel patterns for 'Kerman' and 'Golden Hills', shown in FIG. 14. The area shown is 5 cm×5 cm. 'Kerman' lenticels appear to be distinctly shorter and are more widely spaced on the bark, both horizontally and vertically. The overall impression is that there is more open bark visible. 'Golden Hills' appears to have lenticels that are wide (in the horizontal dimension), and in many cases merge to create horizontal rows. The color of the 'Golden Hills' lenticels was RHS 172C (grey orange) as compared to 'Kerman', for which the color of the lenticels was RHS 172D. The width of the lenticels of 'Golden Hills' ranged from 1.2 to 2.2 mm, with most being about 2 mm in width. The width of the lenticels of 'Kerman' ranged from 1 to about 2 mm, an average of 1.8 to 2.0 mm. The height of the lenticels from both 'Golden Hills' and 'Kerman' was 1 mm.

Flower Buds: Bud size analysis for 'Golden Hills' and 'Kerman' was limited to bud length, since this was the only character that seemed to be different between the varieties. The buds were much thinner than for the males, making width measurements problematic. 10 buds per tree were measured for each of 5 trees. Within tree differences were not found to be highly significant, so data for each cultivar was bulked (eg. 50 buds per cv) and analyzed using a completely random design. As can be seen from the data analysis, bud length differences were highly significant. 'Golden Hills' buds were about 1 mm longer than 'Kerman' buds. (Tables 1 and 2). The color of the emerging inflorescence for both 'Golden Hills' and 'Kerman' was yellow-green (RHS 145C).

TABLE 1

ANOVA TABLE for bud l (mm)

| | DF | Sum of Squares | Mean Square | F-Value | P-Value | Lambda | Power |
|---|---|---|---|---|---|---|---|
| Culitvar | 2 | 25.473 | 12.736 | 25.503 | <.0001 | 51.007 | 1.000 |
| Residual | 147 | 73.411 | .499 | | | | |

Means TABLE for bud l (mm)
Effect: Cultivar

| | Count | Mean | Std. Dev. | Std. Err |
|---|---|---|---|---|
| Golden Hills | 50 | 8.340 | .626 | .089 |
| Kerman | 50 | 7.476 | .643 | .091 |
| Lost Hills | 50 | 8.360 | .832 | .118 |

TABLE 2

| | Mean Diff. | Crit. Diff. | P-Value |
|---|---|---|---|
| Fisher's PLSD for bud l (mm)<br>Effect: Cultivar<br>Significance Level: 5% | | | |
| Golden Hills, Kerman | .864 | .279 | <.0001 S |
| Golden Hills, Lost Hills | −.020 | .279 | .8877 |
| Kerman, Lost Hills | −.884 | .279 | <.0001 S |
| Scheffe for bud l (mm)<br>Effect: Cultivar<br>Significance Level: 5% | | | |
| Golden Hills, Kerman | .864 | .350 | <.0001 S |
| Golden Hills, Lost Hills | −.020 | .350 | .9900 |
| Kerman, Lost Hills | −.884 | .350 | <.0001 S |

Figure 1:
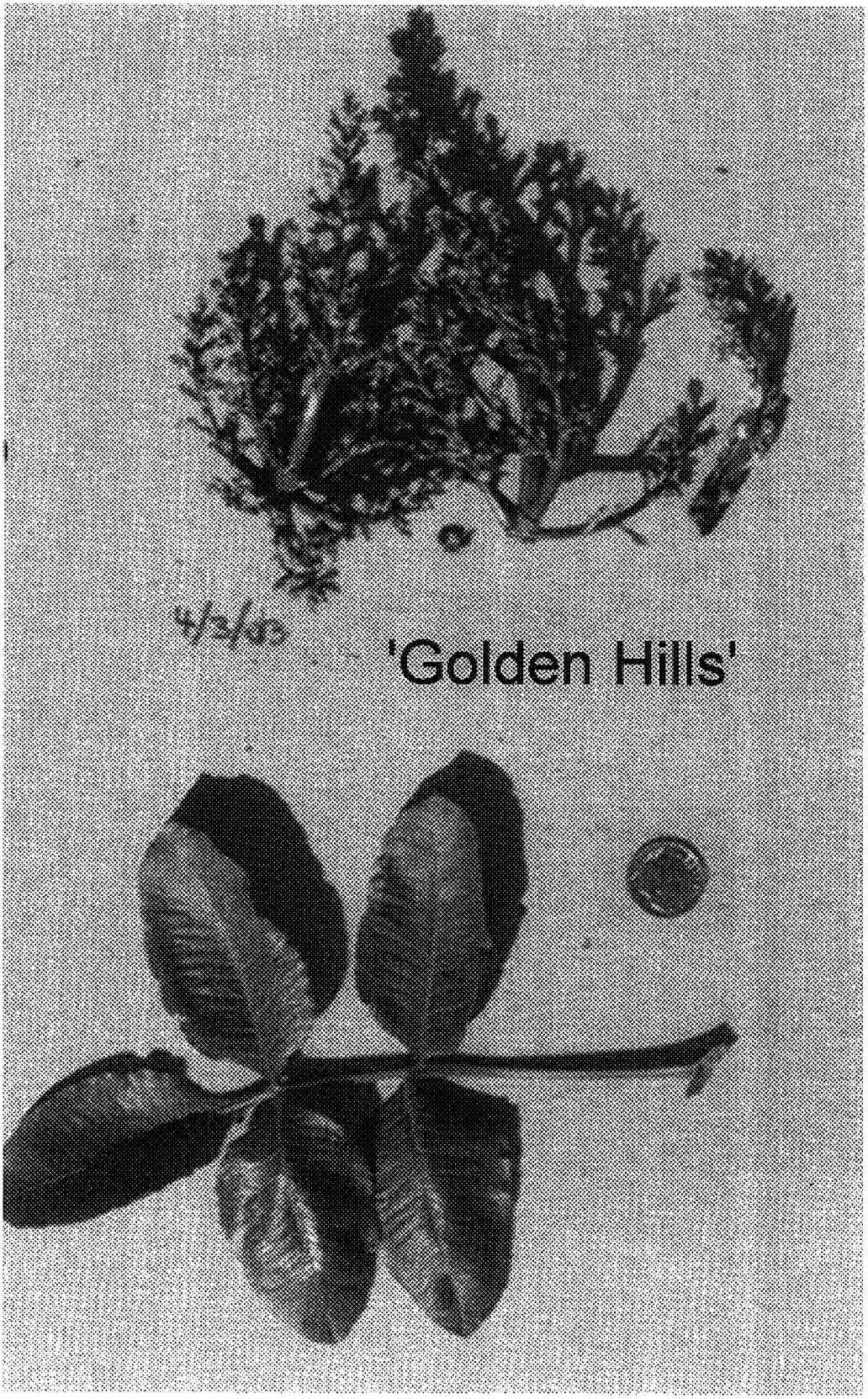
FIG. 1. Flowers and leaves from grafted 'Golden Hills' trees at the Bakersfield test plot in 2003.
Figure 3:
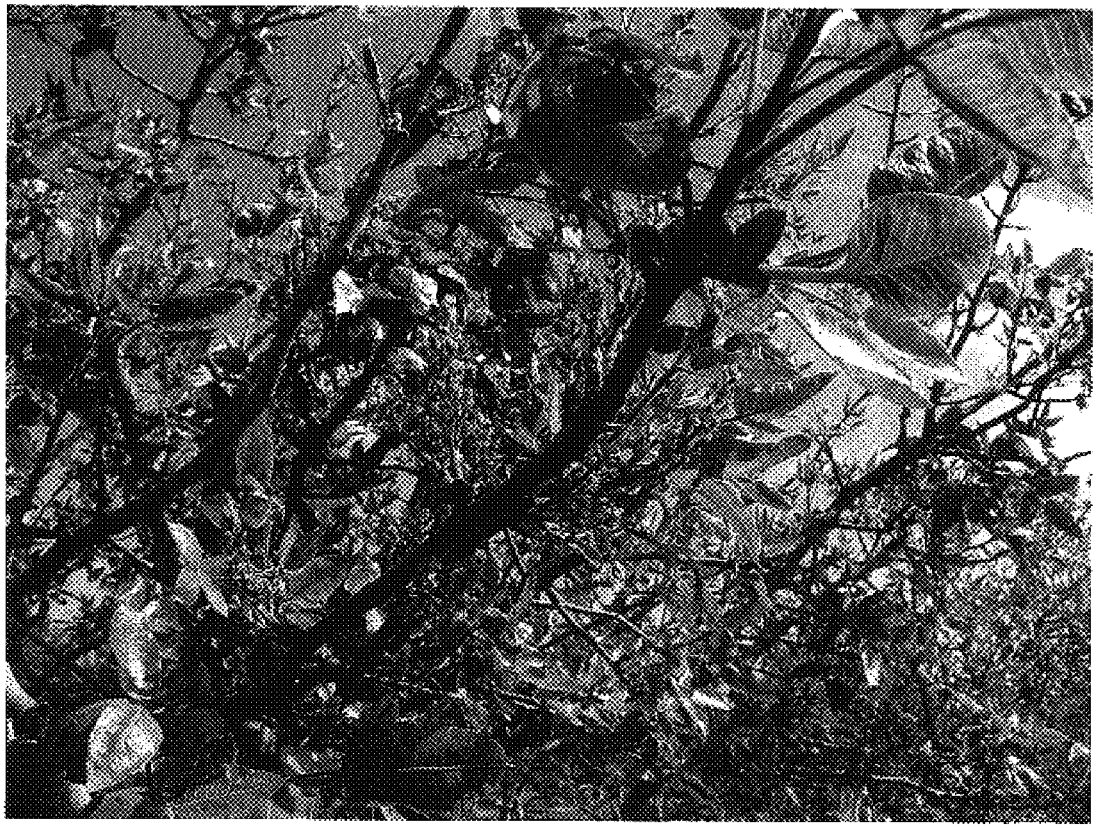
FIG. 3. 'Kerman' flowers—Mar. 31, 2004, mid-bloom. Note that leafing is more advanced than for 'Golden Hills' even though flowering is later.
Figure 4:
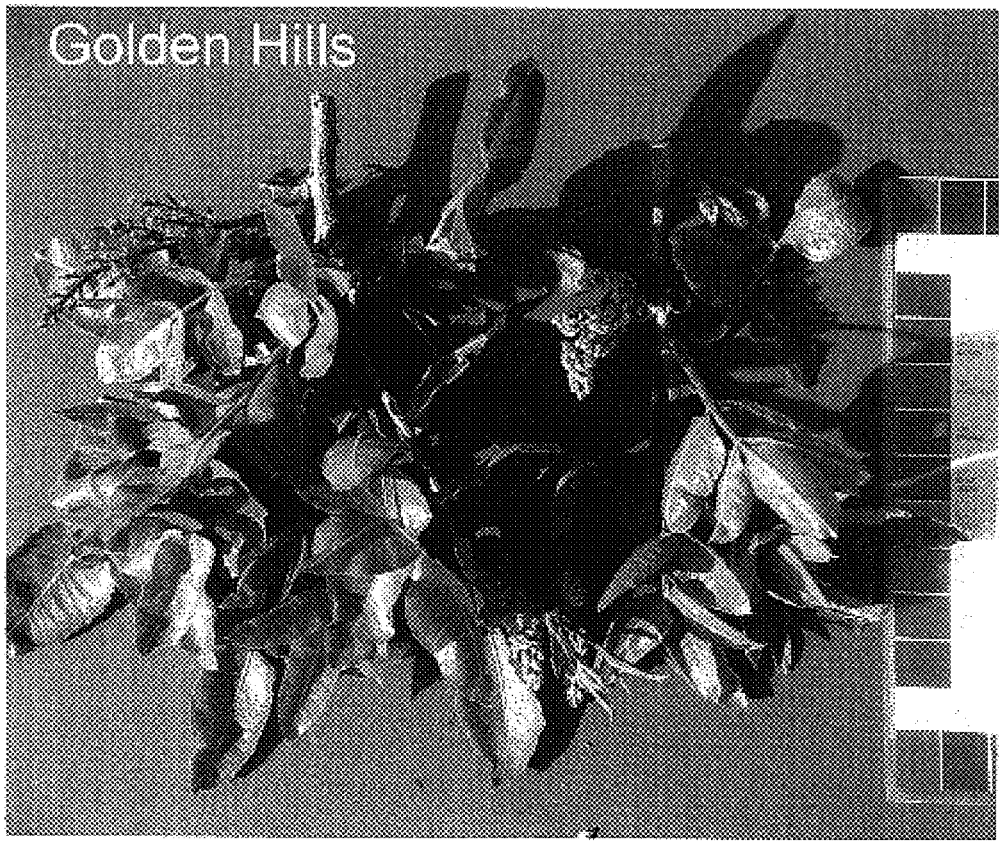
FIG. 4. Comparison of 'Golden Hills' and 'Kerman' leaves and flowers—Mar. 31, 2004.
Figure 4:
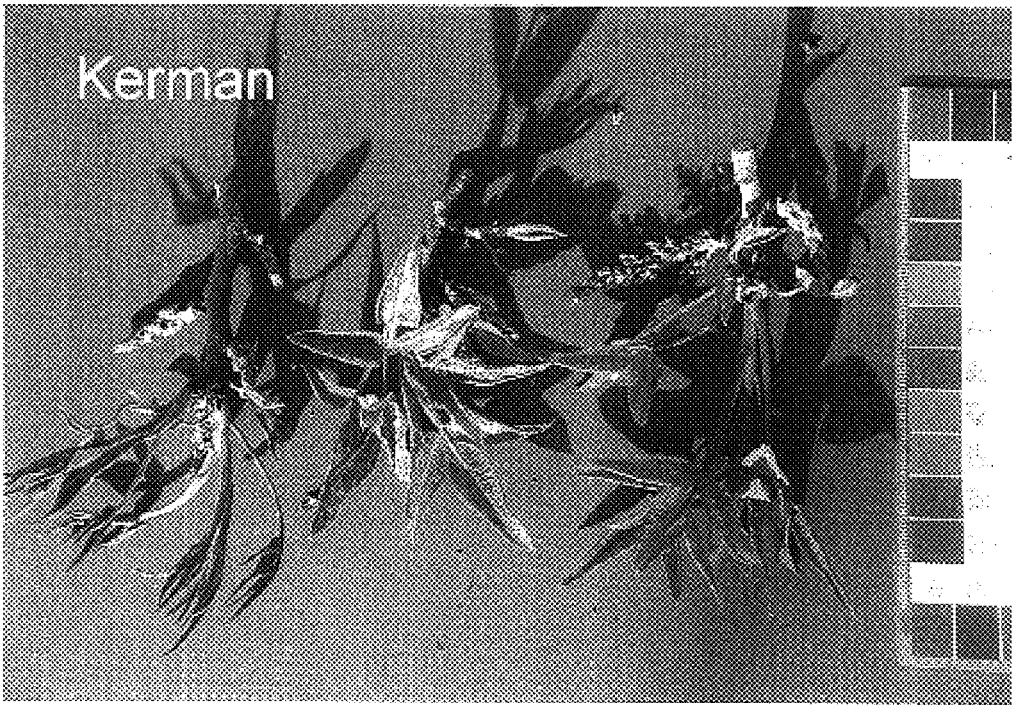

Inflorescences: Female inflorescences are born laterally alternately on branches, rarely as terminal buds. They are located on one year old wood. The flower buds form a branched compound inflorescence of the panicle form. Individual flowers are about 1 mm in size. All flowers are female. The panicles are 5 to 8 cm long with considerable variation in size. The panicles become more extended as flowering progresses. Flowers become receptive from the base to the tip of the panicle, and the total period of receptivity may span a 3 week period, depending on weather conditions during individual seasons. Flowers are pale green (RHS 143C) as are the supporting structures of the panicles (FIGS. 1, 2 and 4). Comparisons with 'Kerman' are provided in FIGS. 3 and 4.

Flowering Date:

Data from seedling test plot in Kern County, Calif.:

1996: For 'Golden Hills'—Apr. 15, 1996

1997: For 'Golden Hills'—first flowering Apr. 15, 1997 to Apr. 21, 1997, peak flowering Apr. 22, 1997 to Apr. 28, 1997, last flowering Apr. 29, 1997 to May 5, 1997; for 'Kerman'—first flowering Apr. 22, 1997 to Apr. 28, 1997, peak flowering Apr. 29, 1997 to May 5, 1997, last flowering—May 6, 1997 to May 13, 1997

1998: For 'Golden Hills'—first flowering Apr. 12, 1998 to Apr. 19, 1998, peak flowering Apr. 20, 1998 to Apr. 27, 1998, last flowering Apr. 20, 1998 to Apr. 27, 1998; for 'Kerman'—first flowering Apr. 20, 1998 to Apr. 27, 1998, peak flowering Apr. 28, 1998 to May 5, 1998, last flowering May 6, 1998 to May 13, 1998.

1999: For 'Golden Hills'—first flowering Mar. 27, 1999 to Mar. 30, 1999, peak flowering Apr. 1, 1999 to Apr. 4, 1999, last flowering Apr. 5, 1999 to Apr. 9, 1999.

2000: For 'Golden Hills'—first flowering Apr. 8, 2000 to Apr. 13, 2000.

Data from grafted test plot in Kern County: Trees were grafted on either 'UCB1' or 'Pioneer Gold-1' rootstocks. Visits to the two experimental sites were made at intervals of three to four days through the bloom period. In 2004 ($8^{th}$ year since grafting), a bloom-rating of 1 through 6 was used with 1=dormant; 2=early bloom, 3=mid bloom, 4=full bloom and 5=late bloom. Bloom evaluation is subjective; the number of individual flowers in bloom within an inflorescence varies, as does the degree of flowering at different locations along a branch. Full bloom was an estimate of when the maximum number of receptive stigmas were present on the tree. On Mar. 25, 2004 'Golden Hills' was at full or mid bloom (3.0), 'Kerman' was just beginning to break buds (1.5).

Leaves: The leaves are single parapinnate compound leaves with an average number of leaflets of 3 or 5. The apex of the leaflet blades is obtuse to cuspidate, and the leaflet base is rounded. Leaflet margins are entire to slightly crenate. Leaflets are oval to ovate. Terminal leaflet appears mucronate in some situations. Leaflets are typically 3–5 cm wide and 4 to 7 cm long. The compound leaf is typically 10 to 15 cm long. There is considerable variation in leaf and leaflet size depending on the time of the season, position in the tree, and year. The width of a compound leaf ranges from 8 to 14 cm. The length of the compound leaf ranges from 10 to 15 cm. Margins of leaf blades are entire. Leaf surfaces are glabrous, smooth and waxy. The color of the upper and lower surfaces of the leaves range from light green at first emergence (RHS 136A to RHS 139B) to dark green at maturity (RHS 136A to RHS 136A). The upper surfaces of the leaves of 'Kerman' range from RHS 136A to RHS 139A at emergence to maturity. (FIGS. 1, 2, and 4). The leaf vein and petiole of 'Golden Hills' are a light yellowish green in color (RHS149D). The petiole is 4 to 7 cm in length and the texture is smooth, with no wings.

Leafing date: In general 'Golden Hills' flowers before leaves start to push, while flowering and leafing are more synchronous with 'Kerman'.

1997: for 'Golden Hills'—first leafing Apr. 22, 1997 to Apr. 29, 1997; for 'Kerman' Apr. 22, 1997 to Apr. 29, 1997.

1998: for 'Golden Hills'—first leafing Apr. 20, 1998 to Apr. 27, 1998; for 'Kerman' Apr. 20, 1998 to Apr. 27, 1998

1999: for 'Golden Hills'—first leafing Apr. 1, 1999 to Apr. 4, 1999

2000: for 'Golden Hills'—first leafing Apr. 8, 2000 to Apr. 13, 2000

Figure 5:
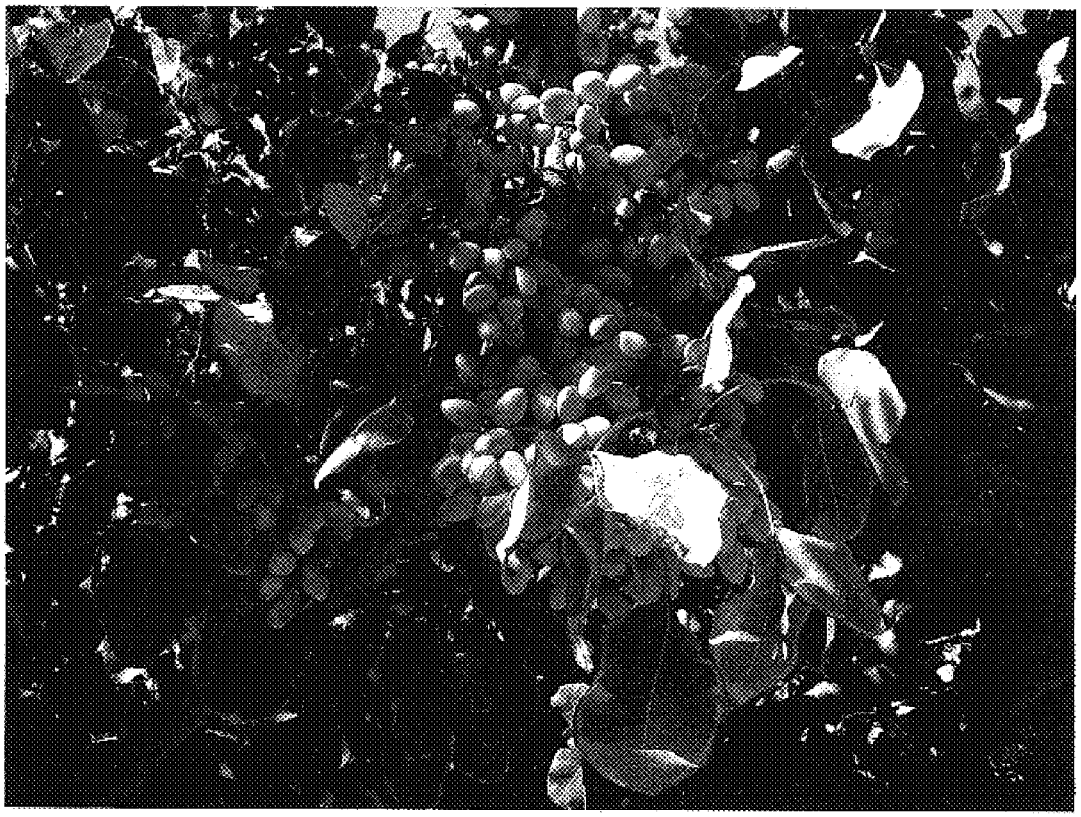
FIG. 5. Fruit clusters on 'Golden Hills' tree at Bakersfield plot, 2003.
Figure 7:
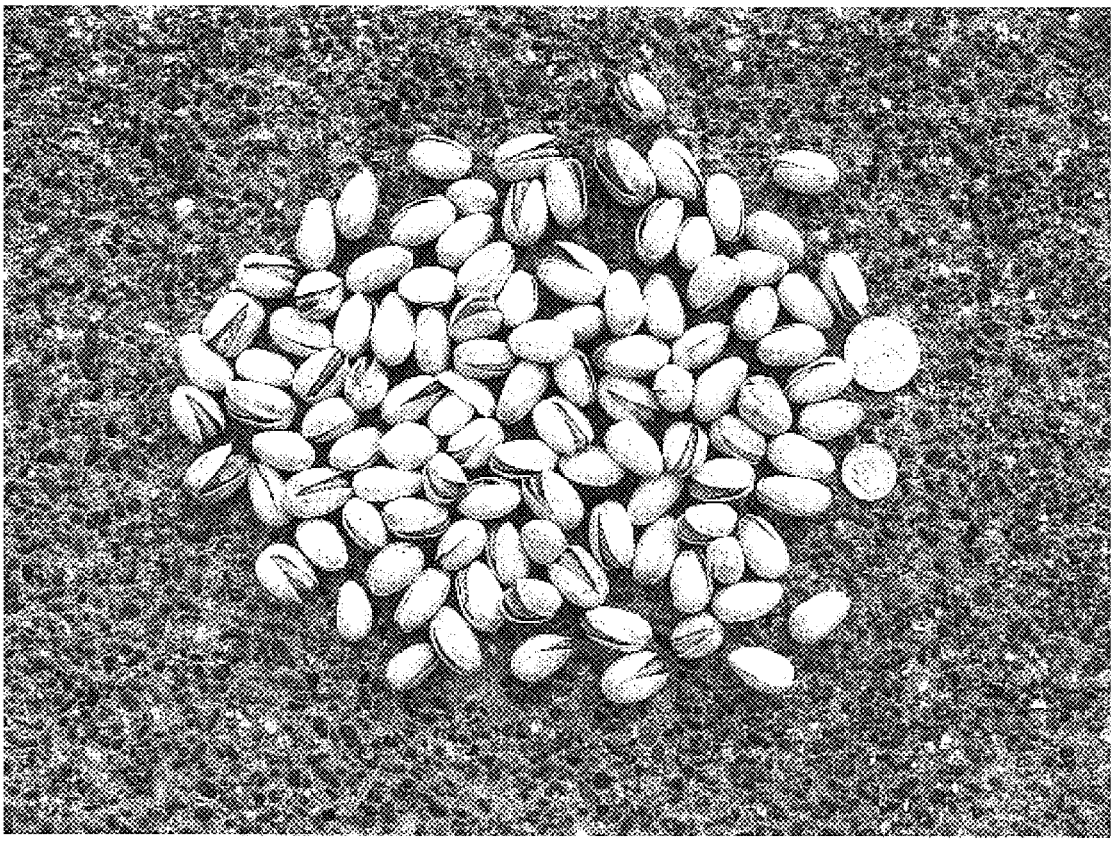
FIG. 7. Roasted seed harvested from 'Golden Hills' grafted trees in the Bakersfield plot, 2003.
Figure 8:
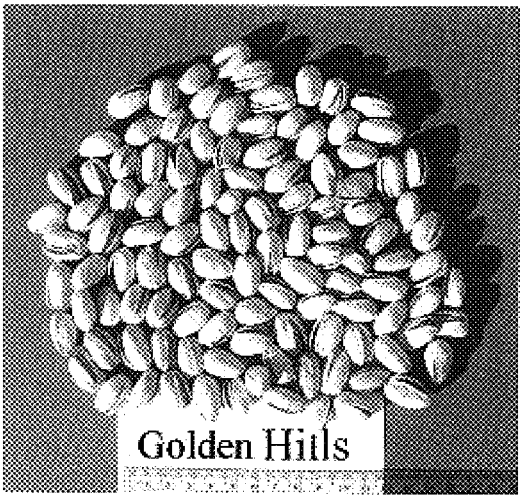
FIG. 8. 'Golden Hills' and 'Kerman' roasted nuts.
Figure 8:
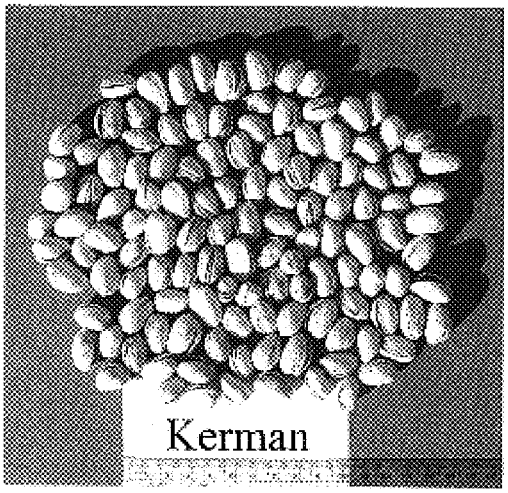
Figure 9:
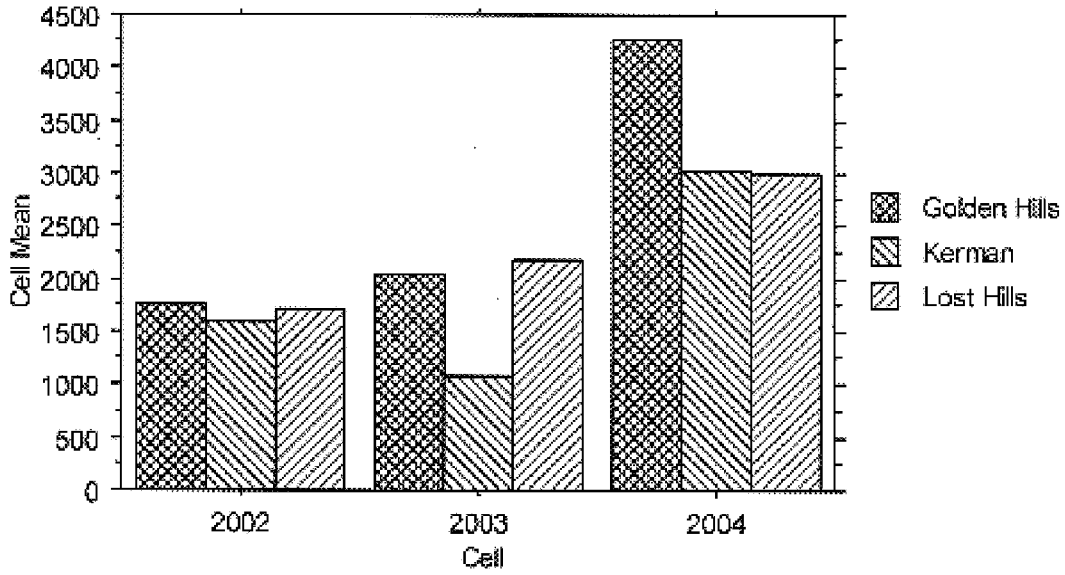
FIG. 9. Year by variety mean values for total yield (CCP assessed weight).
Figure 10:
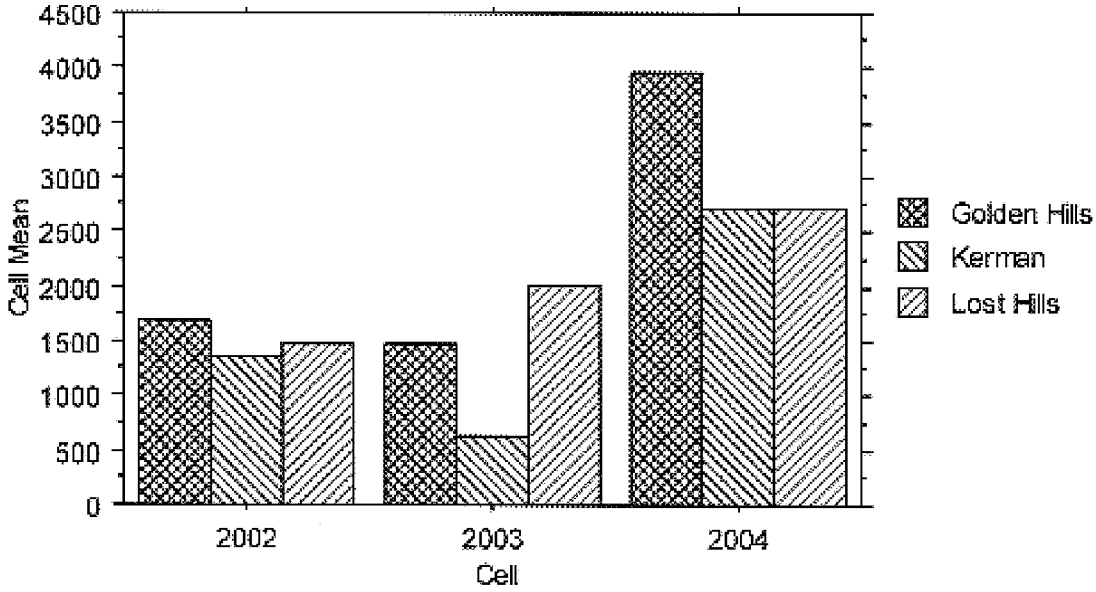
FIG. 10. Year by variety mean values for yield of split nuts.
Figure 11:
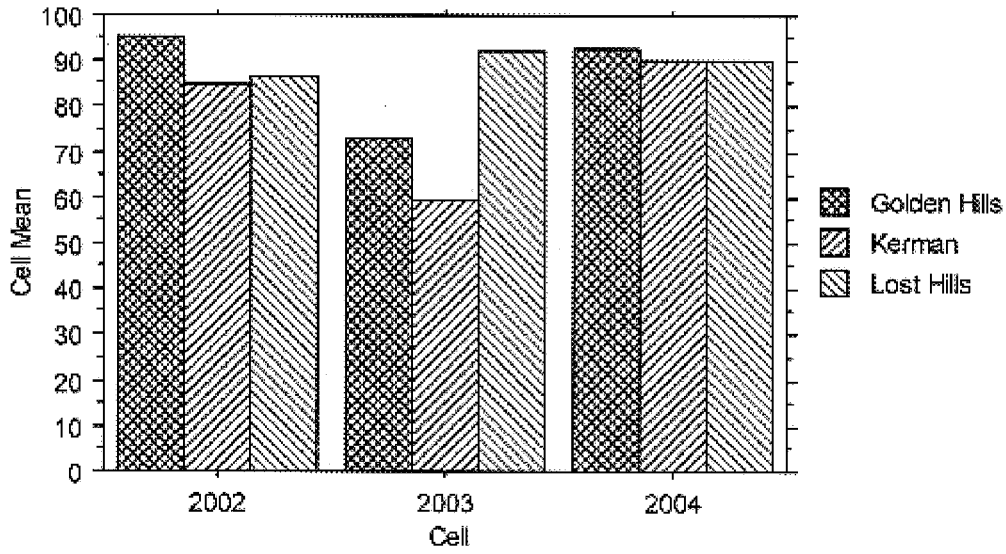
FIG. 11. Year by variety mean values for yield of % split nuts—untransformed data.
Figure 12:
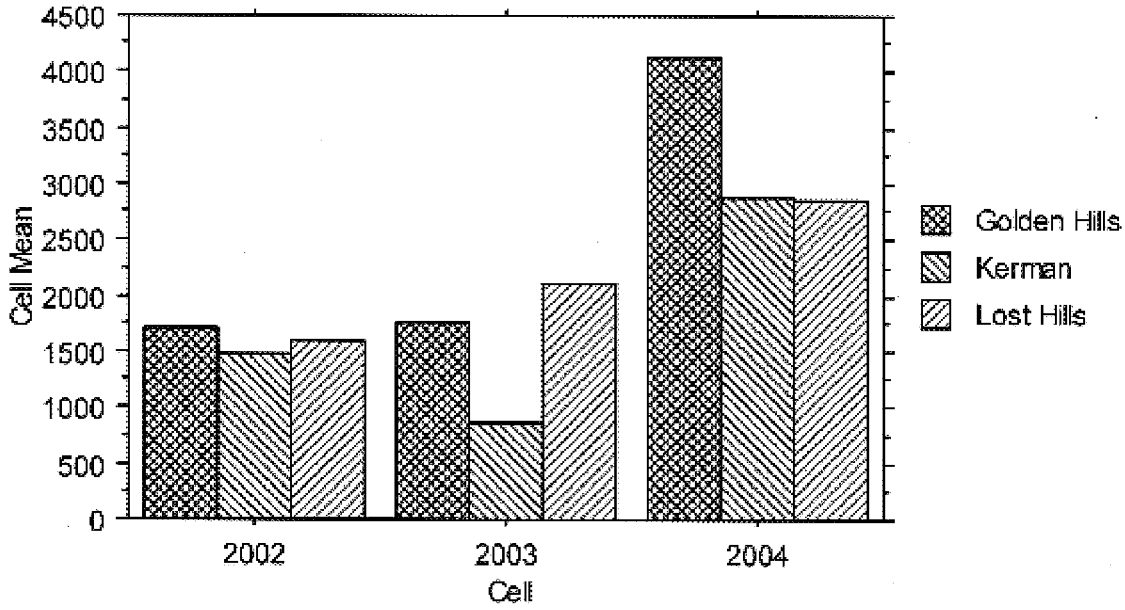
FIG. 12. Year by variety mean values for grower paid yield.

Nut description: Nuts are arranged in panicle clusters (FIG. 5). They are considered drupes. Most flowers abort so that 10 to 20 nuts per cluster remain. The color of the pellicle for both 'Golden Hills' and 'Kerman' is grey-orange (RHS 177D). The pellicle is approximately 0.1 mm in thickness. Husk color gradually changes from a light green in late June to a creamy white, tinged red, color (RHS 52D (pink) to RHS 11D) prior to harvest (FIG. 5). The surface texture of the hull is smooth and dull, with roughness aproximately equivalent to 1000 grit sandpaper. The hull thickness ranges between 1 and 1.5 mm. Husks (exo-mesocarp) initially adhere tightly to the shell (endocarp) but become detached but intact at harvest. Past harvest the husks split, exposing the shell. Shells split midseason, usually 4 to 6 weeks prior to harvest. Some shells do not split, producing a nut with low economic value. This is an important commercial character. Blank nuts are formed when the embryo aborts but the shell and husk continue to develop. Blank nuts are commercially undesirable and do not contribute to yield. 'Golden Hills' produces a processed nut that is very similar to 'Kerman' in size and color. Nuts are oval, longer than wide with a somewhat truncate base and slightly cuspidate to rounded tip (FIG. 7). The shell suture is deep, extending from the tip almost to the base and is symmetrical. 'Kerman' nuts are slightly shorter than 'Golden Hills' nuts (Table 3) and are less symmetrical (FIG. 8). Shell sutures are less symmetrical and a significant percentage of in-shell nuts have a flattened shape with longer shell sutures on one side, not typical for 'Golden Hills'. The color of the 'Golden Hills' kernel is green (RHS 145C), as is the kernel of 'Kerman' (RHS 145 A). The average kernel size is 1.99 cm in length, 1.03 cm in width, and 1.06 cm in depth. The form of the kernel is generally egg shaped or ovate, narrowing toward the micropylar end. The surface texture of the kernel is smooth, with surface wrinkles oriented in a linear manner from the stem end to the micropylar end. The average weight of the kernel is 0.7 grams. The flavor of the kernel is typical of pistachios, similar to 'Kerman', and is slightly sweet and nutty.

TABLE 3

Average individual nut length and width[1] of nuts for 'Golden Hills' and 'Kerman' 'PG-1' rootstock from a test plot in northwestern Kern County from 2002 through 2004 (7th and 8th leaf).

| | nut length, mm | | nut width, mm | |
|---|---|---|---|---|
| Cultivar | 2003 | 2004 | 2003 | 2004 |
| 'Golden Hills' | 20.2 | 18.2 | 11.9 | 12.8 |
| 'Kerman' | 17.8 | 17.0 | 12.2 | 12.3 |

[1]In 2003 the values in the table were based on one 50 nut sample from each variety. In 2004 the values in the table were based on one 50 nut sample from each of the two replicates of each variety.

Split nut percentages (at Kern Co. location unless otherwise noted):

2002: 'Golden Hills'=96%; 'Kerman'=85%

2003: 'Golden Hills'=73% 'Kerman'=60%

2004: 'Golden Hills'=93%; 'Kerman'=90%

2004 at Madera plot: 'Golden Hills'=65%; 'Kerman'=59%

Blank nut percentages (at Kern Co. location unless otherwise noted):

Cumulative 2002–2004: 'Golden Hills'=3.4%; 'Kerman'=24.2%

Harvest date: 'Golden Hills' matures 2 to 4 weeks earlier than 'Kerman' (Table 4). This is a valuable commercial character as it permits growers to better the manage the harvest which otherwise occurs over a short time period. Delayed harvest can also result in high levels of insect (Navel Orangeworm) damage and associated aflatoxin contamination.

TABLE 4

Harvest dates for 'Golden Hills' and 'Kerman' on 'PG1' rootstock from a test plot in northwestern Kern County from 2002 through 2004 (6th through 8th leaf).

| Cultivar | 2002[1,2] | 2003[1] | 2004 |
|---|---|---|---|
| 'Golden Hills' | September 4 | September 3 | August 16 |
| 'Kerman' | September 4 | September 19 | September 21 |

[1]Oil applied in February of 2002 and 2003 to promote earlier bloom in the surrounding orchard (and also in the test plot).
[2]In 2002, 'Golden Hills' was harvested 2+ days past maturity due to scheduling difficulties.

Insect damage: Cumulative insect damage on nuts was 0.0% for 'Golden Hills' and 9.3% for 'Kerman' from 2002 through 2004.

TABLE 19

Additional harvest timing, yield and nut quality information (2002 and 2003) for 'Golden Hills' compared to 'Kerman' on 'PG-1' rootstock. Data from Kern County Plot from different sampling than shown below.

| | 2002 | | 2003 | |
|---|---|---|---|---|
| Characteristic | 'Kerman' | 'Golden Hills' | 'Kerman' | 'Golden Hills' |
| nut yield (CPC weight (5% moisture), lbs/tree | 12.8 | 13.5 | 8.0 | 15.7 |
| split edible in-shell, lbs/tree | 10.0 | 12.4 | 4.7 | 11.0 |
| edible in-shell split percentage | 78 | 92 | 52 | 70 |
| loose shell and kernel percentage | 1 | 1 | 0 | 1 |
| closed shell percentage | 20 | 6 | 46 | 30 |
| blank nuts (no kernel) percentage | 7 | 3 | 6 | 4 |
| individual nut weight (grams) | 1.44 | 1.44 | 1.25 | 1.31 |
| approximate date ready for harvest | 9/4/02 | 9/2/02 | 9/16/03 | 9/3/03 |

Yield: 'Golden Hills' had significantly greater total yield and grower paid yield (after non-split nuts and insect damaged nuts are accounted for) than did 'Kerman'. Cumulative yields for 'Golden Hills' from 2002 through 2004 were about 40% to 45% greater than for 'Kerman'. (FIGS. 9–12).

Total yield in lbs/acre:

2002: 'Golden Hills'=1762; 'Kerman'=1593

2003: 'Golden Hills'=2048; 'Kerman'=1081

2004: 'Golden Hills'=4276; 'Kerman'=3032

Yield of split nuts in lbs/acre:

2002: 'Golden Hills'=1677; 'Kerman'=1355

2003: 'Golden Hills'=1484; 'Kerman'=641

2004: 'Golden Hills'=3969; 'Kerman'=p2725

Grower paid yield in lbs/acre:

2002: 'Golden Hills'=1720; 'Kerman'=1474

2003: 'Golden Hills'=1767; 'Kerman'=861

2004: 'Golden Hills'=4123; 'Kerman'=2876

Values for total yield, inshell yield, and grower paid yield are presented in Table 5.

TABLE 5

Cumulative nut yields[1] for 'Golden Hills' and 'Kerman' on 'PG-1' rootstock from a test plot in northwestern Kern County from 2002 through 2004 (6th through 8th leaf).

| Cultivar | CPC assessed weight, lbs./acre | Edible split inshell nuts, lbs./acre | Grower-paid yield[2], lbs./acre |
|---|---|---|---|
| 'Golden Hills' | 8087 | 7130 | 7609 |
| 'Kerman' | 5707 | 4721 | 5211 |

[1]Yields based on two replications of 10 trees each. Trees were on 'PG-1' rootstock.
[2]Grower-paid yield is the weight of harvested nuts for which the grower is paid. This yield is basically the CPC assessed weight minus the weight of the shells from closed shell and shelling stock.

Evaluation data from the Madera County Test plot is presented in Table 6. This data is relatively preliminary, representing only the first harvestable yield. As was true at the Kern County location, split nut percentages were higher for 'Golden Hills', blank nut percentages were lower for 'Golden Hills', and nut weights were similar to 'Kerman'. Tables 7–18 provide more data on the yield of 'Golden Hills' as compared to both 'Kerman' (unpatented) and 'Lost Hills' (U.S. patent application Ser. No. 11/086,616).

TABLE 6

Nut characteristics for three advanced selections and 'Kerman' on 'PG-1' and 'UCB1' rootstock in a test plot located in southern Madera County, 2004

| Variety | split nut % | adhering hull, % | black nuts, % | loose shell and kernel, % | average nut weight[1], grams |
|---|---|---|---|---|---|
| 'Kerman' | 59.4 | 10.6 | 13.8 | 3.7 | 1.29 |
| 'Golden Hills' | 65.4 | 10.7 | 9.0 | 5.9 | 1.29 |

[1]Based on 50 nut samples.

TABLE 7

ANOVA for total yield (CCP assessed weight). Years, varieties, and interactions were significant.

| | DF | Sum of Squares | Mean Square |
|---|---|---|---|
| year | 2 | 11657142.111 | 5828571.056 |
| variety | 2 | 1888152.111 | 944076.056 |
| year * variety | 4 | 1710508.889 | 427627.222 |
| Residual | 9 | 1020624.500 | 113402.722 |

| | F-Value | P-Value | Lambda | Power |
|---|---|---|---|---|
| year | 51.397 | <.0001 | 102.794 | 1.000 |
| variety | 8.325 | .0090 | 16.650 | .880 |
| year * variety | 3.771 | .0455 | 15.083 | .668 |

TABLE 8

Total yield means table (lbs/acre CCP assessed weight) for varieties × years.

| | Count | Mean | Std. Dev. | Std. Err. |
|---|---|---|---|---|
| 2002, Kerman | 2 | 1593.500 | 88.388 | 62.500 |
| 2002, Lost Hills | 2 | 1707.500 | 67.175 | 47.500 |
| 2002, Golden Hills | 2 | 1762.500 | 540.937 | 382.500 |
| 2003, Kerman | 2 | 1081.500 | 55.861 | 39.500 |
| 2003, Lost Hills | 2 | 2185.000 | 537.401 | 380.000 |
| 2003, Golden Hills | 2 | 2048.500 | 386.787 | 273.500 |
| 2004, Kerman | 2 | 3032.000 | 52.326 | 37.000 |
| 2004, Golden Hills | 2 | 2998.000 | 345.068 | 244.000 |
| 2004, Golden Hills | 2 | 4276.000 | 390.323 | 276.000 |

TABLE 9

Mean differences for yield (CCP assessed weight), protected LSDs, and Scheffe tests (5% significance) for varieties. 'Golden Hills' had significantly higher yield than 'Kerman' at the 1% significance level. 'Lost Hills' had higher yields than 'Kerman', but only at the 7.3% level and lower yield than 'Golden Hills', also at the 7% level. S denotes significant difference at 5%.

| | Mean Diff. | Crit. Diff. | P-Value | |
|---|---|---|---|---|
| | LSD | | | |
| Golden Hills, Kerman | 793.333 | 439.819 | .0028 | S |
| Golden Hills, Lost Hills | 398.833 | 439.819 | .0705 | |
| Kerman, Lost Hills | −394.500 | 439.819 | .0730 | |
| | Scheffe | | | |
| Golden Hills, Kerman | 793.333 | 567.273 | .0090 | S |
| Golden Hills, Lost Hills | 398.833 | 567.273 | .1780 | |
| Kerman, Lost Hills | −394.500 | 567.273 | .1836 | |

TABLE 10

ANOVA for split nut yields. Years, varieties, and interactions were significant.

| | DF | Sum of Squares | Mean Square |
|---|---|---|---|
| year | 2 | 11502633.333 | 5751316.667 |
| variety | 2 | 1966566.333 | 983283.167 |
| year * variety | 4 | 2154286.333 | 538571.583 |
| Residual | 9 | 866340.500 | 96260.056 |

| | F-Value | P-Value | Lambda | Power |
|---|---|---|---|---|
| year | 59.748 | <.0001 | 119.495 | 1.000 |
| variety | 10.215 | .0048 | 20.430 | .938 |
| year * variety | 5.595 | .0153 | 22.380 | .848 |

TABLE 11

Split nut yields means table (lbs/acre) for varieties × years.

| | Count | Mean | Std. Dev. | Std. Err. |
|---|---|---|---|---|
| 2002, Kerman | 2 | 1355.000 | 171.120 | 121.000 |
| 2002, Lost Hills | 2 | 1474.000 | 65.054 | 46.000 |
| 2002, Golden Hills | 2 | 1677.500 | 478.711 | 338.500 |
| 2003, Kerman | 2 | 641.000 | 106.066 | 75.000 |
| 2003, Lost Hills | 2 | 2016.500 | 504.167 | 356.500 |
| 2003, Golden Hills | 2 | 1484.000 | 216.375 | 153.000 |
| 2004, Kerman | 2 | 2725.500 | .707 | .500 |
| 2004, Golden Hills | 2 | 2707.500 | 327.390 | 231.500 |
| 2004, Golden Hills | 2 | 3968.500 | 429.214 | 303.500 |

TABLE 12

Mean differences, protected LSDs, and Scheffe tests (5% significance) for varieties (split nut yields). Both 'Lost Hills' and 'Golden Hills' had significantly higher yields of split nuts than 'Kerman' at the 1% significance level. S denotes significant difference at 5%.

| | Mean Diff. | Crit. Diff. | P-Value |
|---|---|---|---|
| | LSD | | |
| Golden Hills, Kerman | 802.833 | 405.215 | .0015 S |
| Golden Hills, Lost Hills | 310.667 | 405.215 | .1169 |
| Kerman, Lost Hills | −492.167 | 405.215 | .0226 S |
| | Scheffe | | |
| Golden Hills, Kerman | 802.833 | 522.641 | .0051 S |
| Golden Hills, Lost Hills | 310.667 | 522.641 | .2732 |
| Kerman, Lost Hills | −492.167 | 522.641 | .0645 |

TABLE 13

ANOVA for % split nuts (transformed data). Years, varieties, and interactions were significant.

| | DF | Sum of Squares | Mean Square | F-Value | P-Value | Lambda | Power |
|---|---|---|---|---|---|---|---|
| year | 2 | 11.297 | 5.649 | 23.416 | .0003 | 46.832 | 1.000 |
| variety | 2 | 5.627 | 2.813 | 11.663 | .0032 | 23.325 | .964 |
| year * variety | 4 | 11.524 | 2.881 | 11.943 | .0012 | 47.771 | .995 |
| Residual | 9 | 2.171 | .241 | | | | |

TABLE 14

Mean % split nuts (lbs/acre) for varieties × years - untransformed data.

| | Count | Mean | Std. Dev. | Std. Err. |
|---|---|---|---|---|
| 2002, Kerman | 2 | 84.866 | 6.031 | 4.265 |
| 2002, Lost Hills | 2 | 86.317 | .414 | .293 |
| 2002, Golden Hills | 2 | 95.507 | 2.152 | 1.521 |
| 2003, Kerman | 2 | 59.602 | 12.886 | 9.112 |
| 2003, Lost Hills | 2 | 92.241 | .387 | .274 |
| 2003, Golden Hills | 2 | 72.743 | 3.172 | 2.243 |
| 2004, Kerman | 2 | 89.904 | 1.528 | 1.081 |
| 2004, Lost Hills | 2 | 90.280 | .529 | .374 |
| 2004, Lost Hills | 2 | 92.737 | 1.573 | 1.112 |

2004, Golden Hills

TABLE 15

Mean differences, protected LSDs, and Scheffe tests (5% significance) for varieties (% split nuts - transformed data). Both 'Lost Hills' and 'Golden Hills' had significantly higher yields of split nuts than 'Kerman' at the 1+% significance level. 'Lost Hills' and 'Golden Hills' were not significantly different with respect to split nut percentages. S denotes significant difference at 5%.

| | Mean Diff. | Crit. Diff. | P-Value |
|---|---|---|---|
| | LSDs | | |
| Golden Hills, Kerman | .051 | .041 | .0187 S |
| Golden Hills, Lost Hills | −.016 | .041 | .4090 |
| Kerman, Lost Hills | −.067 | .041 | .0047 S |
| | Scheffe | | |
| Golden Hills, Kerman | .051 | .052 | .0542 |
| Golden Hills, Lost Hills | −.016 | .052 | .6976 |
| Kerman, Lost Hills | −.067 | .052 | .0149 S |

TABLE 16

ANOVA for grower paid yield. Years, varieties, and interactions were significant.

| | DF | Sum of Squares | Mean Square |
|---|---|---|---|
| year | 2 | 11536201.444 | 5768100.722 |
| variety | 2 | 1925492.111 | 962746.056 |
| year * variety | 4 | 1888457.889 | 472114.472 |
| Residual | 9 | 924545.000 | 102727.222 |

| | F-Value | P-Value | Lambda | Power |
|---|---|---|---|---|
| year | 56.150 | <.0001 | 112.299 | 1.000 |
| variety | 9.372 | .0063 | 18.744 | .916 |
| year * variety | 4.596 | .0269 | 18.383 | .763 |

TABLE 17

Grower paid yield means table (lbs/acre) for varieties × years.

| | Count | Mean | Std. Dev. | Std. Err. |
|---|---|---|---|---|
| 2002, Kerman | 2 | 1474.000 | 130.108 | 92.000 |
| 2002, Lost Hills | 2 | 1591.000 | 66.468 | 47.000 |
| 2002, Golden Hills | 2 | 1720.500 | 509.824 | 360.500 |
| 2003, Kerman | 2 | 861.500 | 24.749 | 17.500 |
| 2003, Lost Hills | 2 | 2099.500 | 519.723 | 367.500 |
| 2003, Golden Hills | 2 | 1766.500 | 301.395 | 213.500 |
| 2004, Kerman | 2 | 2875.500 | 21.920 | 15.500 |
| 2004, Lost Hills | 2 | 2853.000 | 336.583 | 238.000 |
| 2004, Golden Hills | 2 | 4122.500 | 409.415 | 289.500 |

TABLE 18

Mean differences, protected LSDs, and Scheffe tests (5% significance) for varieties (grower paid yield). Both 'Lost Hills' and 'Golden Hills' had significantly higher grower paid yield of split nuts than 'Kerman' at the 5% significance level. 'Golden Hills' had higher grower paid yield than 'Lost Hills' at the 9% significance level. S denotes significant difference at 5%.

| | Mean Diff. | Crit. Diff. | P-Value |
|---|---|---|---|
| | LSDs | | |
| Golden Hills, Kerman | 799.500 | 418.605 | .0019 S |
| Golden Hills, Lost Hills | 355.333 | 418.605 | .0870 |
| Kerman, Lost Hills | −444.167 | 418.605 | .0399 S |
| | Scheffe | | |
| Golden Hills, Kerman | 799.500 | 539.912 | .0064 S |
| Golden Hills, Lost Hills | 355.333 | 539.912 | .2133 |
| Kerman, Lost Hills | −444.167 | 539.912 | .1079 |

Chilling Requirement: This variety has less of a chilling requirement for dormancy as compared to 'Kerman' resulting in more uniform spring foliation, flowering, pollination and maturity at harvest.

Disease resistance and susceptibility: Earlier harvest resulted in significantly less navel orangeworm damage (0.0% vs. 9.3%). This is an important characteristic since nut damage on the tree is associated with aflatoxin contamination.

Usage: The nuts are primarily sold as a dry "in shell" product for direct consumption at the retail level. They may be sold either "salted" or "unsalted". They are marketed either in packages or are sold in bulk. Small quantities may be used in confections or ice cream. The shipping quality of the nut is excellent, and is similar to Kerman when the husk is removed and the nut is dried. The nut may be stored dry (<6% moisture) at room temperature for up to one year, before exhibiting off-type or stale flavor.

'Golden Hills' is a female tree with a harvest date 2 to 4 weeks earlier than 'Kerman', which is the industry standard. 'Golden Hills' produces a greater yield and higher percentage of split, edible nuts than 'Kerman' while maintaining a similar low percentage of loose shells and kernels. The earlier harvest date will permit growers to extend their harvest period and reduce competition for scarce harvesting resources and may reduce disease in the northern production areas of the state by permitting an earlier harvest before fall rains. The cultivar requires less chilling than 'Kerman', which improves uniformity of foliation, bloom, nut set, nut fill, and uniformity of nut maturity at harvest in years with insufficient chilling for 'Kerman'. Based on all of our evaluations, this cultivar appears to be an exceptional producer and has the potential to increase grower profits by up to 40%, while being better adapted to low chill years, more uniform harvest period, and having fewer Navel Orangeworm problems.

What we claim is:

1. A new and distinct variety of pistachio tree substantially as shown and described herein.

* * * * *